United States Patent [19]

Perenyi et al.

[11] Patent Number: 5,151,419
[45] Date of Patent: Sep. 29, 1992

[54] COMPOSITION FOR THE TREATMENT OF SCHIZOPHRENIA

[75] Inventors: Andras Perenyi, Budapest, Hungary; Goswami Utpal, Calcutta, India; Mihály Arató, Budapest, Hungary; Ede Frescka, Budapest, Hungary; József Knoll, Budapest; D. Arpad Béla, Gyongyos, Hungary

[73] Assignee: Chinoin Gyogyszer- ES Vegyeszeti Termekek Gyara Rt., Budapest, Hungary

[21] Appl. No.: 536,658

[22] PCT Filed: Aug. 17, 1989

[86] PCT No.: PCT/HU89/00044

§ 371 Date: Jun. 18, 1990

§ 102(e) Date: Jun. 18, 1990

[87] PCT Pub. No.: WO90/01928

PCT Pub. Date: Mar. 8, 1990

[30] Foreign Application Priority Data

Aug. 17, 1988 [HU] Hungary .............................. 4374/88

[51] Int. Cl.[5] .................. A61K 31/54; A61K 31/135; A61K 31/445

[52] U.S. Cl. ................................. 514/226.2; 514/317; 514/646

[58] Field of Search ...................... 514/646, 226.2, 317

[56] References Cited

PUBLICATIONS

Parsad, E., Rakodd, V.: Use of Drugs in Psychiatry, A Handbook, Hans Huber Publ., Toronto, 1987, p. 3.
Bernstein, J. G., Handbook of Drug Therapy in Psychiatry, Second Ed., PSG Publishing Co., Inc., Littleton, MA (1988), pp. 112–113.
Chem. Abst. 113-145354e (1990) refers to 1988 article.

Primary Examiner—S. J. Friedman
Attorney, Agent, or Firm—Herbert Dubno; Jonathan Myers

[57] ABSTRACT

The present invention is related to a pharmaceutical composition suitable for the treatment of schizophrenia comprising an acid addition salt of (1)-N-(1-phenyl-isopropyl)-N-methyl-1-propynyl-amine in a therapeutically effective amount and optionally one or more neuroleptica and pharmaceutically acceptable carriers, and other excipients.

6 Claims, No Drawings

COMPOSITION FOR THE TREATMENT OF SCHIZOPHRENIA

The present invention relates to the treatment of schizophrenia characterized by negative symptoms by selegiline (1-Deprenyl) (−)-N-(1-phenylisopropyl)-N-methyl-propynylamine and to a composition for this treatment.

About one third of the schizophrenic patients amounting to 1% of the total population is characterized by negative symptoms, i.e. said patients suffer from schizophrenia of type II. according to Crow., i.e. they loose interest about themselves and their environment, their cognitive function gets damaged and their orientation to the future is characterized by ambivalence and ambitendency. The conventional neuroleptica as such are not successful, on the other hand, they may be harmful due to their side effects. (Ideggyógyászati Szemle 1983, Psych. Res. 1984.)

Several compounds were tested for the treatment of these patients in order to find an effective drug and in order to be able to send home the patients treated for a long time in mental social homes.

Morphological changes are supposed to be observed in schizophrenic patients characterized by negative symptoms. (Brit. J. Psych. 1980, Brit. Med. J. 1983. Psychopharmacology Basic Aspects 1980, Schizophr. Bull. 1982, Arch. Gen. Psych. 1982, Arch. Gen. Psych. 1982, Arch. Gen. Psych. 1986.)

It is known that within the nerve system the dopamine hypofunction is in connection with the Parkinson disease (Klin. Wschr. 1960.) leading to the treatment with 1-DOPA (Canad. med. Ass. J. 1969.). But the increase of the dopaminerg tone concerning the whole organism, was accompanied by several side effects (hypertonic crisis, tremor, gastrointestinal disorders etc.).

It is further known that 1-deprenyl inhibits the monoamino-oxydase-B (MAO-B) enzyme, i.e. it acts as dopamine agonist (Arch. Intern. Pharmacodyn. 1965.).

Schizophrenia is characterized according to our present knowledge by the hyperactivity of the mesocortical system, which can be located mainly to the nucleus accumbens. This hyperactivity is decreased by neuroleptica. Post-mortem investigations have proved that the number of dopamine receptors of the above brain parts increases upon long neuroleptic treatment. (A pszichiátria alapjai, Akadémia Kiadó Budapest 1986. p. 168.).

On the basis of this knowledge it could not be expected that selegiline is suitable for the treatment of schizophrenia.

The psychiatric indications of the successfully tested selegiline are given on the basis of the New Haven Schizophrenia index, the Carpenter-Strauss-Bartko WHO Flexible System and the DSM III systems. In each case the precondition is the confirmation of the diagnosis of the schisophrenia and the exclusion of organic, toxic (drug, alcohol), affective pathological forms.

Considering these results the selegiline is suggested for the following symptoms: slow and almost symptomless beginning, deficiency in impulses, introversion, lack of rapport ability, hesitating speech, poor associations, insensibility, asthenia, lack of feeling of joy, instinct dynamical fading, poor social and working connections, isolation.

The group of symptoms can appear at the beginning of the pathological process of schisophrenia or at its subchronic or chronic period as well.

Selegiline is applied at a daily dosage of 10–50 mg on each occasion at 5–10 mg, preferably orally or intramuscularly. It may be administered together with one or more neuroleptica. It is suggested to carry on with the treatment for at least one month, but depending on the condition of the patient the treatment may be prolonged for a longer period.

The used selegiline can be prepared by methods disclosed in HU PS 154 655 and 187 775. The most preferred drug forms are the tablets and capsules.

Neuroleptica are a group of compounds defined in the Dictionary of Pharmacology (Blackwell Scientific. Publ. Oxford 1985, p. 143), the best known representatives of this group are chlorpromazine, thioridazine, flufenazine, haloperidol and pimozide. The maintaining neuroleptic treatment is carried out with the usual therapeutic doses.

The pharmaceutical compositions according to the invention are prepared by using selegiline and optionally the known neuroleptica by methods known per se.

EXAMPLE 1

In an open test 13 chronic schizophrenic patients were administered selegiline for 6 weeks, and this was followed by a 5 weeks tapering-off period. The dosage was 15 mg/day. The patients were characterized by the chronicity and by the negative symptoms, by the lack of positive symptoms, they were selected on the basis of these symptoms.

The changes of the psychic condition were followed by the following methods: Brief Psychiatric Rating Scale (Overall and Gorham 1962.), Nurses Observation Scale for Inpatient Evaluation (Guy, W.: ECDEU Assessment Manual for Psychopharmacology. Department of Health Education and Welfare Publication No. 76-338. Superintendent of Documents U.S. Government Printing Office, Washington D.C., 1976 p.: 266–273) and Negative Symptom Rating Scale (Jager et al., 1985.).

The changes of the possible extrapyramidal symptoms as well as their formation or their ceasing were followed by Abnormal Involuntary Movement Scale see: the Nurses Observation Scale from page 534, and Targeting Abnormal Kinetic Effect (Wojcik et al., 1980, Comprehensive Psychiatry, 21. p. 370).

During the examination none of the patients dropped out. On the Negative Symptom Rating Scale a significant improvement could be observed already after the first week of treatment and this significant improvement could be shown to the end of the treatment until the period after the tapering-off. The patients were treated during the whole examination with the unchanged neuroleptica. The rating was carried out on the 0., 10., 24., 44. day and then after another 5 weeks.

EXAMPLE 2

Preparation of 150 mg tablets 50 g of selegiline-hydrochloride, 30 g of talc, 30 g of magnesium stearate, 90 g of polyvidone, 460 g of starch, 840 g of lactose were admixed by methods known per se, followed by granulation and the mixture was compressed to 150 mg tablets. About 10 000 tablets containing 5 mg selegiline-hydrochloride were prepared.

We claim:

1. A method of treating schizophrenia in a patient characterized by negative symptoms, which comprises administering to said patient, a therapeutically effective amount of (−)-N-(1-phenyl-isopropyl)-N-methyl-propynylamine or a pharmaceutically acceptable acid addition salt thereof.

2. The method of treating schizophrenia defined in claim 1 wherein a therapeutically effective amount of (−)-N-(1-phenyl-isopropyl)-N-methyl-propynylamine in the form of a pharmaceutically acceptable acid addition salt is administered.

3. The method of treating schizophrenia defined in claim 1 wherein a therapeutically effective amount of (−)-N-(1-phenyl-isopropyl)-N-methyl-propynylamine hydrochloride is administered.

4. The method of treating schizophrenia defined in claim 1 wherein 10 to 50 mg per day of (−)-N-(1-phenyl-isopropyl)-N-methyl-propynylamine or a pharmaceutically acceptable acid addition salt thereof is administered.

5. The method of treating schizophrenia defined in claim 1 wherein the treatment is carried out for at least one month.

6. A pharmaceutical composition for the treatment of schizophrenia, which comprises a therapeutically effective amount of (−)-N-(1-phenyl-isopropyl)-N-methyl-propynylamine or a pharmaceutically acceptable acid addition salt thereof, and a therapeutically effective amount of one or more neuroleptica selected from the group consisting of chlorpromazine, thioridazine, flufenazine, haloperidol, and pimozide, and a pharmaceutically acceptable inert carrier.

* * * * *